(12) United States Patent
Bolger et al.

(10) Patent No.: US 6,340,363 B1
(45) Date of Patent: Jan. 22, 2002

(54) IMAGE GUIDED VERTEBRAL DISTRACTOR AND METHOD FOR TRACKING THE POSITION OF VERTEBRAE

(75) Inventors: Ciaran Bolger, Bristol (GB); Anthony J. Melkent, Germantown, TN (US); Kurt R. Smith, Boulder, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/555,885
(22) PCT Filed: Oct. 8, 1999
(86) PCT No.: PCT/US99/23451
  § 371 Date: Sep. 6, 2000
  § 102(e) Date: Sep. 6, 2000
(87) PCT Pub. No.: WO00/21442
  PCT Pub. Date: Apr. 20, 2000

Related U.S. Application Data
(60) Provisional application No. 60/103,618, filed on Oct. 9, 1998.

(51) Int. Cl.[7] .................................................. A61F 5/04
(52) U.S. Cl. ........................................ 606/90; 606/102
(58) Field of Search ............................. 60/86, 90, 105, 60/102, 130; 600/232, 235

(56) References Cited

U.S. PATENT DOCUMENTS

| | | |
|---|---|---|
| 4,892,545 A | 1/1990 | Day et al. |
| 4,898,161 A | 2/1990 | Grundei |
| 4,899,761 A | 2/1990 | Brown et al. |
| 4,952,214 A | 8/1990 | Comparetto |
| 5,059,194 A | 10/1991 | Michelson |
| 5,147,287 A | 9/1992 | Jewell et al. |
| 5,156,605 A * | 10/1992 | Pursley et al. ............ 606/56 X |
| 5,198,877 A | 3/1993 | Schulz |
| 5,305,203 A | 4/1994 | Raab |
| 5,309,913 A | 5/1994 | Kormos et al. |
| 5,329,933 A * | 7/1994 | Graf |
| 5,383,454 A | 1/1995 | Bucholz |
| 5,389,101 A | 2/1995 | Heilbrun et al. |
| 5,399,146 A | 3/1995 | Nowacki et al. |
| 5,402,801 A | 4/1995 | Taylor |
| 5,437,668 A * | 8/1995 | Aronson et al. .......... 606/56 X |
| 5,447,154 A | 9/1995 | Cinquin et al. |
| 5,483,961 A | 1/1996 | Kelly et al. |
| 5,494,034 A | 2/1996 | Schlöndorff et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,568,809 A | 10/1996 | Ben-haim |

(List continued on next page.)

FOREIGN PATENT DOCUMENTS

| | | | |
|---|---|---|---|
| DE | 3722595 A * | 1/1989 | ................ 606/105 |
| DE | 297 04 393 | 8/1997 | |
| SU | 001132932 A * | 1/1985 | ................ 606/102 |
| WO | WO 96/11624 | 4/1996 | |

*Primary Examiner*—Jeffrey A. Smith
(74) *Attorney, Agent, or Firm*—Harness, Dickey & Pierce, P.L.C.

(57) ABSTRACT

A vertebral distractor is disclosed for use in performing anterior cervical spinal surgery. The vertebral distractor is associated with a computer controlled surgical navigation system employing an energy-detecting array to track positions of the vertebral distractor in three dimensional space relative to a known reference point. The guide comprises a shaft, a stationary first arm, and at least one movable second arm. At least one electrically energizable energy emitter array is attached to the shaft for use in identifying the location of the vertebral distractor relative to the vertebrae. A system for using the vertebral distractor in spinal surgery is disclosed.

26 Claims, 5 Drawing Sheets

U.S. PATENT DOCUMENTS

| | | |
|---|---|---|
| 5,572,999 A | 11/1996 | Funda et al. |
| 5,588,430 A | 12/1996 | Bova et al. |
| 5,603,318 A | 2/1997 | Heilbrun et al. |
| 5,617,857 A | 4/1997 | Chader et al. |
| 5,622,170 A | 4/1997 | Schulz |
| 5,630,431 A | 5/1997 | Taylor |
| 5,638,819 A | 6/1997 | Manwaring et al. |
| 5,647,361 A | 7/1997 | Damadian |
| 5,662,111 A | 9/1997 | Cosman |
| 5,676,673 A | 10/1997 | Ferre et al. |
| 5,682,886 A | 11/1997 | Delp et al. |
| 5,695,500 A | 12/1997 | Taylor et al. |
| 5,695,501 A | 12/1997 | Carol et al. |
| 5,711,299 A | 1/1998 | Manwaring et al. |
| 5,748,767 A | 5/1998 | Raab |
| 5,749,362 A | 5/1998 | Funda et al. |
| 5,755,725 A | 5/1998 | Druais |
| 5,772,594 A | 6/1998 | Barrick |
| 5,795,294 A | 8/1998 | Luber et al. |
| 5,799,055 A | 8/1998 | Peshkin et al. |
| 5,800,535 A | 9/1998 | Howard, III |
| 5,823,958 A | 10/1998 | Truppe |
| 5,833,608 A | 11/1998 | Acker |
| 5,834,759 A | 11/1998 | Glossop |
| 5,836,954 A | 11/1998 | Heilbrun et al. |
| 5,848,967 A | 12/1998 | Cosman |
| 5,851,183 A | 12/1998 | Bucholz |
| 5,868,675 A | 2/1999 | Henrion et al. |
| 5,871,445 A | 2/1999 | Bucholz |
| 5,871,487 A | 2/1999 | Warner et al. |
| 5,891,157 A | 4/1999 | Day et al. |
| 5,904,691 A | 5/1999 | Barnett et al. |
| 5,920,395 A | 7/1999 | Schulz |
| 5,921,992 A | 7/1999 | Costales et al. |

\* cited by examiner

IMAGE GUIDED VERTEBRAL DISTRACTOR AND METHOD FOR TRACKING THE POSITION OF VERTEBRAE

Applicants claim the right to priority based on Provisional Patent Application No. 60/103,618 filed Oct. 9, 1998.

FIELD OF THE INVENTION

The present invention relates generally to providing a vertebral distractor for adjusting, particularly increasing, the distance between two vertebrae along the spinal axis when performing spinal procedures, particularly in the anterior cervical region, in conjunction with systems that use and generate images during medical and surgical procedures, which images assist in executing the procedures and indicate the relative position of various body parts and surgical instruments.

BACKGROUND OF THE INVENTION

Vertebral distractors are known and are tools used during a spinal procedure, such as an anterior cervical procedure. Generally, the tool is used to increase the distance between two vertebral elements, such as vertebrae in a patient's neck for the removal of damaged bone and/or the insertion of a bone graft into the damaged area. In particular, a vertebral distractor has two arms mounted in parallel on a shaft. The arms are movable in relation to each other.

To remove damaged bone and/or insert a bone graft, the arms of the vertebral distractor are engaged with or attached to different cervical vertebrae in the neck area. Certain vertebral distractors have arms with sharpened ends for gripping or otherwise engaging the vertebrae. The vertebrae are then pulled apart in a generally axial direction by manually increasing the distance between the arms of the distractor. While the vertebrae are distracted, the tension in the connecting soft tissues provides interbody rigidity. While the vertebrae remain distracted, surgical procedures can be performed, such as for example, damaged bone can be removed and new bone can be inserted.

During an anterior cervical spinal procedure, the vertebral distractor is positioned on either side of the throat area. In some cases, more than one vertebral distractor is used and is positioned such that there is a distractor on each side of the throat. This allows for more even distraction of the vertebrae. In positioning the vertebral distractor and engaging with or attaching it to the vertebrae of the patient, and, further, in completing the anterior cervical spinal surgery, the surgeon may have limited visual ability to determine the exact position of the vertebral distractor or the vertebrae with which the arms of the distractor are engaged.

Computer assisted image guided surgical navigation systems have been described that include indications of the relative positions of medical instruments and body parts used in medical or surgical procedures. For example, U.S. Pat. No. 5,383,454 to Bucholz; PCT Application No. PCT/US94/04530 (Publication No. WO 94/24933) to Bucholz; and PCT Application No. PCT/US95/12894 (Publication No. WO 96/11624) to Bucholz et al., the entire disclosures of which are incorporated herein by reference, disclose systems for use during a medical or surgical procedure using scans generated by a scanner prior to the procedure. Surgical navigation systems typically include tracking element such as for example an LED or reflector array on the body part and the medical instruments, a digitizer to track the positions of the body part and the instruments, and a display for the position of an instrument used in a medical procedure relative to a body part.

SUMMARY OF THE INVENTION

Accordingly, the present invention is directed to a vertebral distractor and a system for using a vertebral distractor in performing anterior surgery, particularly cervical spinal surgery. More specifically, an object of the present invention is directed to an apparatus for distraction or maintaining the relative position of at least two vertebrae in the cervical spinal area in conjunction with an image guided surgery system.

To achieve this object and other advantages and in accordance with the purpose of the invention, as embodied and broadly described herein, the invention includes a vertebral distractor for use in performing anterior cervical spinal surgery. The vertebral distractor is used in conjunction with a computer controlled surgical navigation system employing a position sensing unit to track positions of the vertebral distractor in three dimensional space relative to a known reference point. The vertebral distractor comprises a shaft having first and second arms attached to the shaft movable with respect to each other. The first and second arms are engageable with the vertebrae, such as by gripping or pinning. Moreover, the second arm is movable with relation to the first arm as the arms are engaged with the vertebrae for adjusting the distance between the vertebrae. At least one tracking array is attached to the shaft for tracking the location of the vertebral distractor as it is used to increase the distance between the vertebrae. One preferred tracking array includes tracking elements such as at least three LEDs.

Moreover, the preferred first and second arms each have extensions located at the distal end for engaging the vertebrae in the cervical spinal region. It is further preferred that the extensions be pins, although other means for gripping known in the art can be used as well.

In yet another aspect, the invention includes a method for adjusting the distance between two vertebrae using the vertebral distractor described above. The method comprises the steps of engaging the vertebral distractor having at least one tracking array which has tracking elements with the vertebrae and then increasing the distance between the vertebrae by moving the second arm away from the first arm. A surgical navigation system with a computer controller and a position sensing unit is employed to communicate with the tracking elements of the tracking array on the vertebral distractor thereby creating a reference point for the vertebral distractor. Further, the location of each individual vertebrae element can be registered by contacting the vertebrae with a trackable instrument such as a registration probe. In a preferred embodiment the optically tracked instrument is a digitizer probe.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in this description.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate one embodiment of the invention and together with the description, serve to explain the principles of the invention.

DETAILED DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts. The following example is intended to be purely exemplary of the invention.

Figure 1:
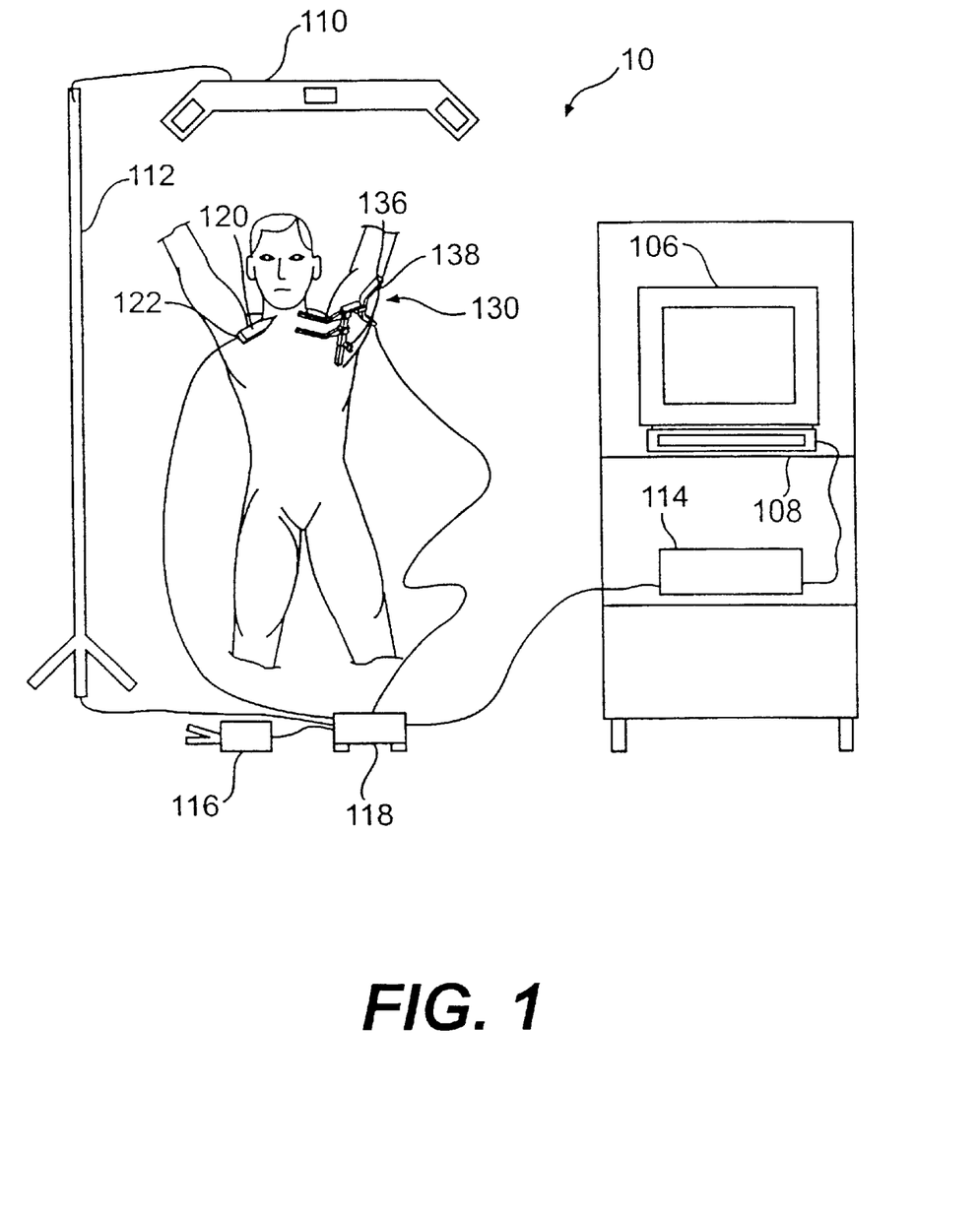
FIG. 1 is a schematic diagram of one preferred embodiment of a system, including a vertebral distractor, a reference arc, and a digitizer for use with a surgical navigation system for spinal surgical procedures.

The vertebral distractor of the present invention is shown generally at 130 in FIG. 1. A vertebral distractor 130 can be used in many known computer assisted image guided surgical navigation systems such as the system shown in FIG. 1 and disclosed in PCT Application No. PCT/US95/12984 (Publication No. WO 96/11624) to Bucholz et al. incorporated herein by reference. A computer assisted image guided surgery system, shown at 10, generates an image for display on a monitor 106 representing the real time position of one or more body parts. A digitizer probe 120, or other tracked instrument, bearing tracking elements such as for example LED emitters 122, is provided for registration of the body parts.

An image may be generated on a monitor 106 from an image data set stored in a controller, such as computer 108, wherein the image is usually generated pre-operatively by some scanning technique such as by a CT scanner or by magnetic resonance imaging. The image data set and the image generated have reference points for at least one body part such as a cervical spinal element. The reference points for the particular body part have a fixed spatial relation to the particular body part.

Figure 2:
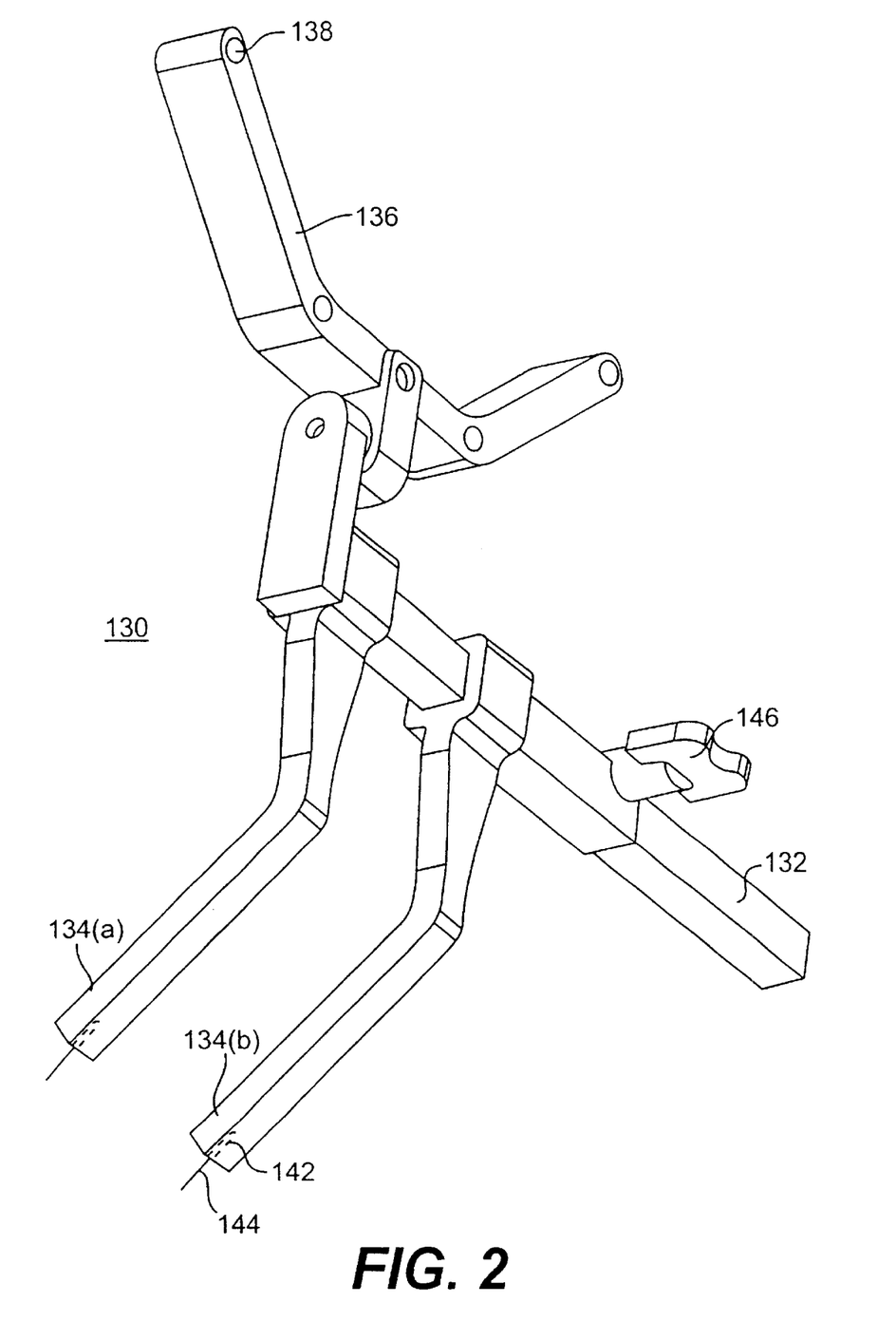
FIG. 2 is a perspective view of one preferred embodiment of a vertebral distractor according to the present invention.

The system 10 also generally includes an apparatus such as a sensor array 110 or other known position sensing unit, that identifies the relative position of each of the reference points during the procedure. The reference points tracked during the procedure are the tracking elements shown as emitters 138, on the tracking array shown as emitter array 136 of the vertebral distractor 130, as shown in FIG. 2. The system also includes a digitizer 114. The digitizer 114 interacts with the controller 108 during the procedure in order to modify the image set according to the identified relative position of each of the reference points during the procedure. The emitter array 136 may generate signals representing the position of the vertebral distractor 130 during the procedure. Alternatively, reflective surfaces as other tracking elements, may be used, instead of LED emitters, to identify the position of the vertebral distractor 130. In other alternative embodiments, sonic or magnetic based tracking devices may be used.

The sensor array 110, mounted on support 112, receives the signals generated by the emitter array 136 in order to identify during the procedure the relative position of each of the reference points and, hence, the vertebral distractor 130 and the body attached thereto. The digitizer 114 and the controller 108 may then modify the image data set according to the identified relative position of each of the reference points during the procedure. The controller 108 may then generate an image data set representing the position of the body parts relative to other tracked surgical instruments. The system 10 may also include a foot switch 116 connected to the vertebral distractor 130 and the digitizer 114 for controlling operation of the system. The structure and operation of an image guided surgery system is well known in the art and need not be discussed further here.

In accordance with the preferred embodiment of the present invention, with further reference to FIG. 2, the invention includes vertebral distractor 130 for use in performing anterior cervical spinal surgery. A vertebral distractor 130 has a shaft 132 for supporting a stationary first arm 134a and at least one movable second arm 134b attached thereto. The shaft 132 and arms 134a and 134b are preferably fabricated of surgical grade material, such as stainless steel, titanium, or aluminum. A vertebral distractor as described above is manufactured by Sofamor Danek and is sold under the trade name Trimline ACDF Distractor.

The image guided vertebral distractor 130 of this invention is used in conjunction with a computer controlled surgical navigation system 10 employing a position sensing unit 110 to track positions of the vertebral distractor 130 in three dimensional space relative to a known reference point. It is preferred that the position sensing unit be an energy-detecting array. An electrically energizable energy emitter array 136 is rigidly attached to the shaft 132 for use in identifying the location of the vertebral distractor 130.

In the preferred vertebral distractor 130 of this invention, as shown in FIG. 2, a stationary arm 134a is rigidly attached to the shaft 132. The stationary arm 143a has an angular configuration as it projects from the shaft 132. A movable arm 134b is movably attached to the shaft 132. The movable arm 134b is in a parallel plane with the stationary arm 134a and is angular in structure as it projects from the shaft 132. The arm 134b is movable in a generally axial direction along the shaft 132, with respect to the stationary arm 134a, via a rack and pinion type system 146. Those of ordinary skill in the art will understand that other types of systems for moving the arms relative to one another may be used, such as a ratchet-type system, lever, or screw drive.

In the embodiment depicted in FIG. 2, it is further preferred that the distal end of each of the arms 134a and 134b define a partial recess 142. It is further preferred that the recess 142 be formed at the center portion of the distal end. In the preferred embodiment shown in FIG. 2, a sharpened protrusion or pin 144 is located in the recess 142 such that a portion of the pin 144 protrudes from the distal end of the arms 134a and 134b. The pins 144 facilitate engagement of the vertebral distractor 130 with the vertebrae. The pins 144 can be held in place by set screws (not shown), clips (not shown), or other holding devices known to those of ordinary skill in the art. One of ordinary skill in the art would also understand that engagement or gripping devices other than pins, such as, for example, arms 134a and 134b narrowed to sharpened points, or hooks or clamps may be used.

The preferred emitter array 136 depicted in FIG. 2 is generally U-shaped. The emitter array 136 is rigidly attached to the shaft 132 of the vertebral distractor 130 with a pin-type connection. In this embodiment, the emitter array 136 lies generally in parallel with the shaft 132. Those of ordinary skill in the art would understand that many other configurations, as well as attachment means, would satisfy the requirements for the emitter array 136. The emitter array 136 is fabricated of surgical grade material such as stainless steel, titanium, aluminum or various plastics. At least three emitters 138 are included in the emitter array structure. In the embodiment depicted in FIG. 2, there are four emitters 138 in the emitter array 136.

Figure 3:
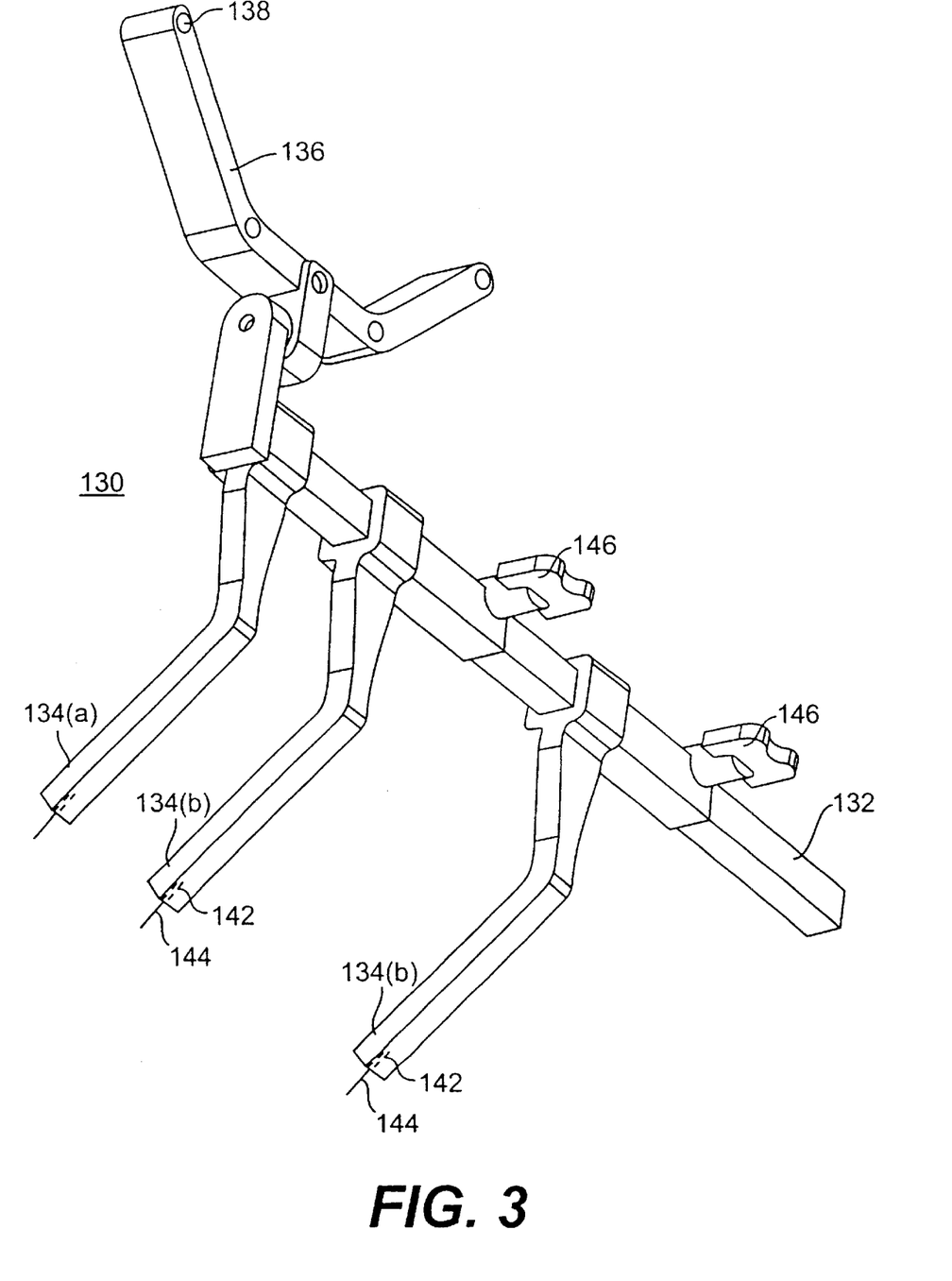
FIG. 3 is a perspective view of another preferred embodiment of the vertebral distractor according to the present invention.

In another embodiment of this invention, as depicted in FIG. 3, the vertebral distractor 130 could have one stationary arm 134a and two movable arms 134b. The arms 134b are movable along the shaft 132 of the vertebral distractor 130 in relation to the stationary arm 134a. In use, the two movable arms 134b and the stationary arm 134a will each be engaged with a separate vertebrae, i.e., three vertebrae in the cervical area can be engaged. Each movable arm 134b is then moved to increase the distance between the vertebrae, thereby distracting the vertebrae. It would be obvious to one skilled in the art that a vertebral distractor 130 is not limited to two movable arms 134b.

As shown in FIG. 2, the emitter array 136 is equipped with a plurality of emitters or other tracking elements, preferably four emitters 138, for generating a signal representing the location of the vertebral distractor 130. In a preferred embodiment, the emitters 138 are light emitting diodes ("LEDs"); however, other tracking devices known in the art that are capable of being tracked by a corresponding sensor array are within the scope of the invention. For purposes of illustration, not limitation, the tracking device may provide signals, acoustic, magnetic, electromagnetic, radiologic, micropulsed radar systems, or reflective surfaces.

A vertebral distractor 130 is used to increase the distance between cervical vertebrae in order to return the length of the cervical spinal area to its pre-injury status. In operation of a preferred embodiment of this invention, the cervical area of the patient is opened to expose the damaged area. The arms 134a and 134b of the vertebral distractor 130 then engage the cervical vertebrae of interest. In the preferred embodiment, the arms 134a and 134b are engaged by inserting the pins 144 located at the distal ends of the arms 134a and 134b into the vertebrae. The space between the arms 134a and 134b is then increased, by moving the movable arm 134b away from the stationary arm 134a, thereby moving the vertebrae to another relative position, such as a pre-injury position. When the vertebrae are returned to their pre-injury position, the structure, including the vertebrae of interest and the disc or discs lying there between, becomes rigid due to tension in the attached soft tissues, such that the structure, i.e., the vertebrae of interest and the disc or discs disposed there between, moves as a single unit.

Figure 5:
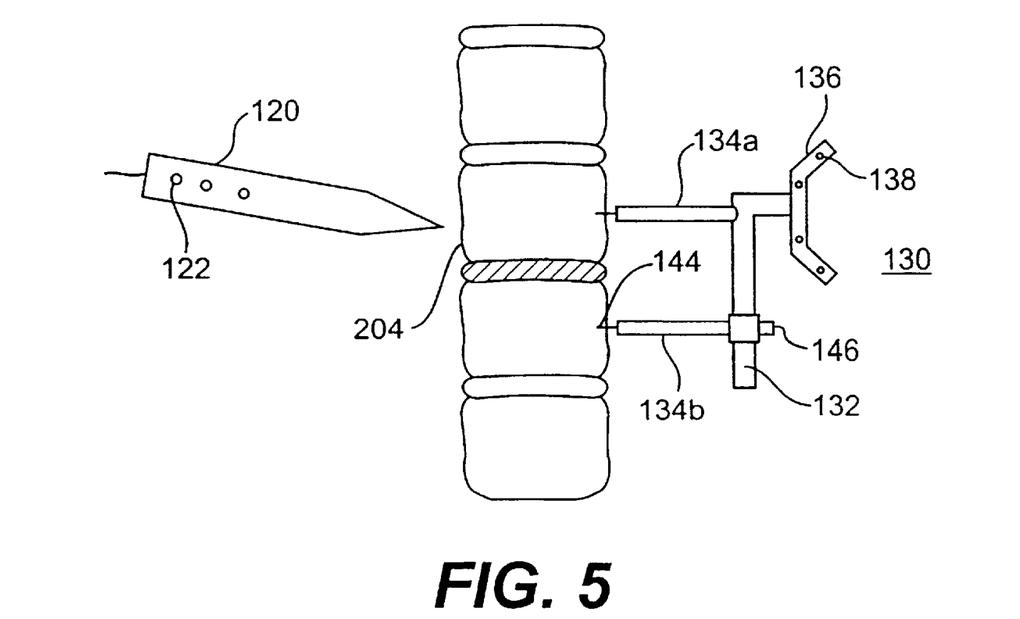
FIG. 5 is a detailed view of a procedure using a preferred embodiment of a vertebral distractor according to the present invention including use of a digitizer probe.

Reference points are then created for the vertebral distractor 130 and the vertebrae to which it is attached. As noted above, the vertebral distractor 130 has an emitter array 136, which provides a reference point for the distractor 130. The reference point for the vertebral distractor 130 is set when the vertebral distractor 130 is engaged with the vertebrae of interest. A reference point for the body is provided by touching the one of the vertebrae of interest in at least three locations with a digitizer probe 120, as shown in FIG. 5. Thus, the image guided surgical system 10 has initial locations for the vertebral distractor 130 and of the vertebrae of interest.

The relationship between the emitter array 136 and the shaft 132 of the vertebral distractor 130 remains constant because the array 136 is rigidly attached to the shaft 132. The stationary arm 134a is also rigidly attached to the shaft 132 and, as a result, the relationship between the array 136 and the stationary arm 134a also remains constant. Because the relationship between the array 136 and the stationary arm 134a is constant, the signals provided by the emitters 138 can be used by the computer assisted image guided surgical navigation system 10 to inform the surgeon of the position of the vertebral distractor 130. Moreover, due to the rigid nature of the vertebrae structure, as discussed above, the movement of the vertebrae will likewise be known by the image guided surgical navigation system 10, as it rigidly relates to the vertebral distractor 130.

Additionally, the invention includes a system for use in performing anterior cervical spinal surgery. The system comprises the above described vertebral distractor 130 and computer controlled surgical navigation system 10 employing a position sensing unit such as an energy detecting array 110 to track positions of the vertebral distractor 130 in three dimensional space relative to a known reference point in a body, i.e., a vertebrae, similarly tracked by a sensor array 110.

The vertebral distractor 130 and the computer controlled surgical navigation system 10 enable the surgeon to see the relative position of anatomy and surgical instruments.

Figure 4A:
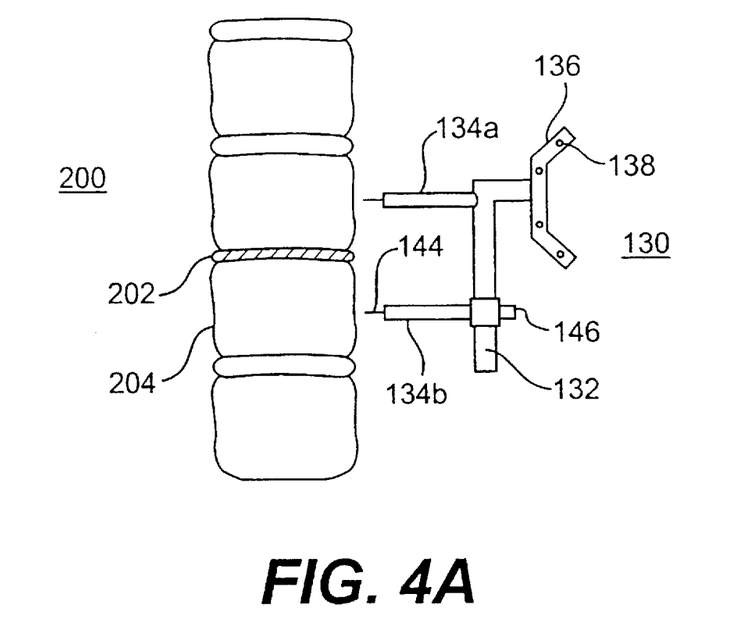
FIGS. 4A, 4B, and 4C are detailed before, during, and after views of a procedure using a preferred embodiment of a vertebral distractor according to the present invention.
Figure 4B:
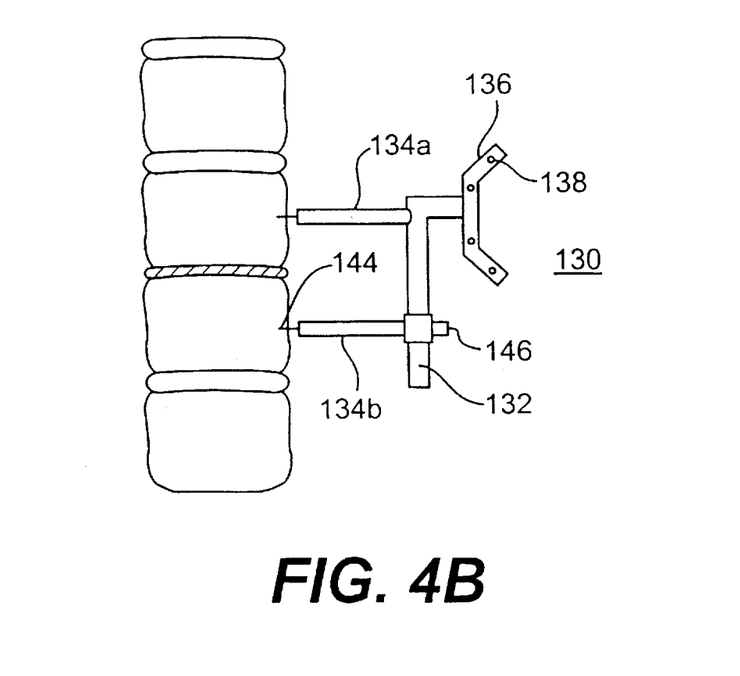
Figure 4C:
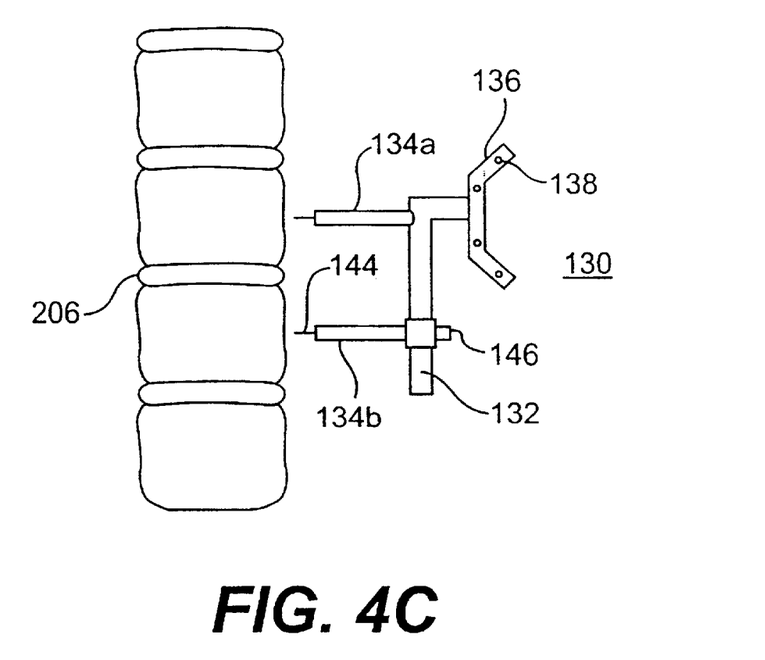

FIG. 4A shows a detailed view of a cervical spinal segment 200 having a damaged disc 202 interposed between two vertebrae 204. To remove the damaged disc 202 and/or to insert a bone graft in its place, it is necessary to restore the cervical area to its pre-injury position by increasing the space between the vertebrae 204 using a vertebral distractor 130 as shown in FIG. 4B. In this position it is possible to remove the damaged disc 202 or insert new bone in the area. FIG. 4C depicts the cervical spinal segment 200 after new bone 206 is inserted into the disc space and the vertebral distractor 130 is removed.

Once the surgeon registers the vertebrae 204 with the computer controlled surgical navigation system 10 by touching the vertebrae 204 in at least three locations with the digitizer probe 120 as depicted in FIG. 5, the location of the vertebrae 204 can be viewed on the computer system so that the surgeon can see in real time the relative location of the vertebral distractor 130 and tracked surgical instruments.

Having described the preferred embodiment of the vertebral distractor 130 used in the present system, the method of using this apparatus to practice the invention will now be described. The operation of a surgical navigating system is generally well known and is described in PCT/US95/12894.

In using the image guided vertebral distractor 130, the first step is to identify the location of the cervical spine using the computer-aided image guided surgical navigation methods. This can be accomplished by performing a preoperative CT scan or magnetic resonance imaging. Once the pre-operative location of the cervical spine is determined, the cervical neck area of the patient is opened, exposing the damaged area. The vertebral distractor 130 is then engaged with the body by pushing the pins 144 of the arms 134a and 134b into the vertebrae of interest, as shown in FIG. 4B, thereby fixing the reference points for the vertebral distractor 130. Ordinarily, the vertebrae of interest must be registered individually in the computer controlled surgical navigation system 10. This is accomplished by first distracting the vertebrae of interest, i.e., increasing the distance between the vertebrae, and then touching the digitizer probe 120 to one of the vertebrae 204. At least three locations on the vertebrae must be registered by the probe 120. The location of the vertebrae 204 is therein entered into the computer 108. If desired, additional vertebrae can thereafter be registered.

The tension in the soft tissues when distracting the vertebrae causes an interbody rigidity in the vertebrae of interest, such that they move as a single unit. This interbody rigidity enables the surgeon to dynamically reference any vertebrae within the arms 134a and 134b of the vertebral distractor 130.

Once the vertebrae 204 is registered with the computer system, the vertebral distractor 130 can be tracked in space by the surgical navigation system 10 without further surgical exposure of the cervical spine. The position of the vertebral distractor 130 is determined by the user stepping on a foot pedal 116 to energize the emitter array 136. The emitters 138 generate infrared signals to be picked up by the energy detecting array 110 and are triangulated to determine the position of the vertebral distractor 130. As the vertebrae 204 is engaged with the vertebral distractor 130, the location of the vertebrae 204 is determined relative to the vertebral distractor. As is well known in this art and described in PCT/US95/12894, based upon the relative position of the cervical spinal segment and the vertebral distractor 130 (such as by touching a known reference point) the computer would illustrate a pre-operative scan—such as the proper CT scan slice—on the screen of the monitor 106 which would indicate the relative position of the cervical spinal segment and tracked surgical instruments.

It will be apparent to those skilled in the art that various modifications and variations can be made in the present invention and in construction of this vertebral distractor in association with a surgical navigation system without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

1. A vertebral distractor for use with a computer controlled surgical navigation system employing a position sensing unit to track positions of said vertebral distractor in three dimensional space relative to a known reference point, said vertebral distractor comprising:

a shaft having a first and a second arm mounted on said shaft, wherein said first and second arms are engageable with vertebrae, and wherein said second arm is movable along said shaft with relation to said first arm while said first and second arms are engaged with said vertebrae; and at least one trackable array rigidly attached to said shaft of said vertebral distractor, wherein said position sensing unit tracks said array and the position of said vertebral distractor while rigidly attached to the vertebrae.

2. The vertebral distractor of claim 1, wherein said first arm is rigidly attached to said shaft and said second arm is movable with respect thereto.

3. The vertebral distractor of claim 1, wherein said first and second arms are engageable with cervical vertebrae.

4. The vertebral distractor of claim 1, wherein said array includes at least three LED emitters.

5. The vertebral distractor of claim 1, wherein said array includes at least three reflector surfaces.

6. The vertebral distractor of claim 1, wherein said shaft has a third arm mounted thereon for engaging at least one vertebrae.

7. The vertebral distractor of claim 1, wherein said first and second arms have extensions located at the distal ends for engaging said vertebral distractor with said vertebrae.

8. The vertebral distractor of claim 7, wherein said extensions are sharpened protrusions for penetrating said vertebrae.

9. The vertebral distractor of claim 1, wherein said position sensing unit is an energy-detecting array.

10. The vertebral distractor of claim 1, wherein said second arm is in a parallel plane with said first arm.

11. The vertebral distractor of claim 1, wherein said position sensing unit is an electromagnetic localization system.

12. A method for tracking the position of vertebrae using a vertebral distractor having first and second arms movable along a shaft in relation to one another, when performing anterior spinal surgery, said method comprising the steps of:

engaging said vertebral distractor having at least one electrically detectable array attached thereto with said vertebrae;

employing a surgical navigation system with a computer controller and a position sensing unit for communicating with said array and tracking the position of said vertebral distractor in three-dimensioned space; and registering the location of said vertebrae relative to said distractor by contacting said vertebrae with a calibration probe tracked by said position sensing unit.

13. The method of claim 12, wherein said emitter array includes at least three LED emitters.

14. The method of claim 12, wherein said shaft has at least two movable arms attached thereto.

15. The method of claim 12, wherein said first and second arms have extensions located at the distal ends for engaging said vertebral distractor with said vertebrae.

16. The method of claim 15, wherein said extensions are pins.

17. The method of claim 12, wherein said probe is a digitizer probe.

18. The method of claim 12, wherein said position sensing unit comprises an energy-detecting unit.

19. The vertebral distractor of 12, wherein said position sensing unit is an electromagnetic localization system.

20. A vertebral distractor comprising:

a stationary arm displacement means and movable arm displacement means, said movable arm displacement means being movable along a shaft in relation to said stationary arm displacement means;

means for tracking the position in three-dimensional space of said vertebral distractor, wherein said tracing means comprises at least one trackable array; and means for registering and tracking the positions of vertebrae, wherein said registering means is an optically tracked unit.

21. The vertebral distractor of claim 20, wherein said tracking means comprises at least three LED emitters.

22. The vertebral distractor of claim 20, further comprising said shaft having at least three arms attached thereto.

23. The vertebral distractor of claim 20, wherein said first and second arm displacement means have gripping means located at the distal ends for engaging said vertebral distractor with said vertebrae.

24. The vertebral distractor of claim 23, wherein said gripping means comprise pins.

25. The vertebral distractor of claim 20, wherein said registering means comprises a digitizer probe.

26. The vertebral distractor of claim 20, wherein said tracking means includes a computer controlled surgical navigation system employing a position sensing unit, wherein said position sensing unit is an energy-detecting array.

* * * * *

UNITED STATES PATENT AND TRADEMARK OFFICE
CERTIFICATE OF CORRECTION

PATENT NO. : 6,340,363 B1
DATED : January 22, 2002
INVENTOR(S) : Ciaran Bolger, Anthony J. Melkent and Kurt R. Smith It is certified that error appears in the above-identified patent and that said Letters Patent is hereby corrected as shown below:

Column 8,
Line 33, after "of" insert -- claim --.
Line 41, "tracing" should be -- tracking --.

Signed and Sealed this

Sixth Day of May, 2003

JAMES E. ROGAN
*Director of the United States Patent and Trademark Office*